US011744924B2

(12) United States Patent
Ashrafi et al.

(10) Patent No.: US 11,744,924 B2
(45) Date of Patent: Sep. 5, 2023

(54) STRETCHABLE NANOCOMPOSITE SKIN MATERIAL AND RELATED STRUCTURES

(71) Applicant: NATIONAL RESEARCH COUNCIL OF CANADA, Ottawa (CA)

(72) Inventors: Behnam Ashrafi, Montreal (CA); Michael Jakubinek, Ottawa (CA); Kurtis Laqua, Welland (CA); Yadienka Martinez-Rubi, Ottawa (CA); Benoit Simard, Ottawa (CA)

(73) Assignee: NATIONAL RESEARCH COUNCIL OF CANADA, Ottawa (CA)

( * ) Notice: Subject to any disclaimer, the term of this patent is extended or adjusted under 35 U.S.C. 154(b) by 736 days.

(21) Appl. No.: 16/613,878

(22) PCT Filed: May 14, 2018

(86) PCT No.: PCT/CA2018/050571
§ 371 (c)(1),
(2) Date: Nov. 15, 2019

(87) PCT Pub. No.: WO2018/209434
PCT Pub. Date: Nov. 22, 2018

(65) Prior Publication Data
US 2020/0101202 A1  Apr. 2, 2020

Related U.S. Application Data

(60) Provisional application No. 62/506,279, filed on May 15, 2017.

(51) Int. Cl.
A61L 27/60 (2006.01)
A61L 27/44 (2006.01)
(Continued)

(52) U.S. Cl.
CPC ............. *A61L 27/60* (2013.01); *A61L 27/443* (2013.01); *A61L 27/446* (2013.01); *B32B 5/14* (2013.01);
(Continued)

(58) Field of Classification Search
CPC ...... A61L 27/60; A61L 27/443; A61L 27/446; A61L 2400/12; B32B 5/266; B32B 5/14;
(Continued)

(56) References Cited

U.S. PATENT DOCUMENTS 6,045,826 A  4/2000 Borowy-Borowski et al.
9,278,856 B2  3/2016 Hunt et al.
(Continued)

FOREIGN PATENT DOCUMENTS

CA  2774987 A1  5/2011
CA  2776999 A1  10/2011
(Continued)

OTHER PUBLICATIONS

H. Koerner et al., Deformation—Morphology correlations in electrically conductive carbon nanotube—thermoplastic polyurethane nanocomposites, Mar. 17, 2005, pp. 1-16, Elsevier Ltd., Dayton, United States of America.
(Continued)

*Primary Examiner* — Forrest M Phillips

(57) ABSTRACT

A stretchable multiple-layer nanocomposite material is provided and includes at least a nanocomposite material layer comprising a network of nanotubes modified with an elastomeric polymer; and at least one additional layer laminated with the nanocomposite material layer. The number of nanocomposite layers and additional layers, the nature and composition thereof, may be varied in a surface direction and/or a thickness direction so as to provide tailored mechanical and physico-chemical properties to a resulting
(Continued)

skin that can be used to produce morphing or deployable structures.

20 Claims, 9 Drawing Sheets

(51) Int. Cl.
*B32B 5/14* (2006.01)
*B32B 5/26* (2006.01)

(52) U.S. Cl.
CPC ........... *B32B 5/266* (2021.05); *A61L 2400/12* (2013.01); *B32B 2260/023* (2013.01); *B32B 2260/046* (2013.01); *B32B 2262/10* (2013.01); *B32B 2262/106* (2013.01); *B32B 2274/00* (2013.01); *B32B 2307/51* (2013.01); *B32B 2307/546* (2013.01); *B32B 2605/18* (2013.01)

(58) Field of Classification Search
CPC ........ B32B 2260/023; B32B 2260/046; B32B 2262/10; B32B 2262/106; B32B 2274/00; B32B 2307/51; B32B 2307/546; B32B 2605/18
See application file for complete search history.

(56) References Cited

U.S. PATENT DOCUMENTS

| | | | |
|---|---|---|---|
| 2007/0213450 | A1 | 9/2007 | Winey et al. |
| 2010/0264376 | A1* | 10/2010 | Korzhenko ............. C08J 3/226 252/511 |
| 2010/0282906 | A1 | 11/2010 | Sanderson et al. |
| 2010/0308279 | A1 | 12/2010 | Zhou et al. |
| 2011/0260116 | A1 | 10/2011 | Plee et al. |
| 2012/0186742 | A1 | 7/2012 | Kang et al. |
| 2015/0147573 | A1* | 5/2015 | Zhang ................... B82Y 10/00 427/113 |
| 2016/0111626 | A1 | 4/2016 | Takagaki et al. |
| 2016/0347461 | A1 | 12/2016 | Hu |
| 2018/0194102 | A1 | 7/2018 | Lima et al. |

FOREIGN PATENT DOCUMENTS

| | | |
|---|---|---|
| CN | 101440208 B | 1/2011 |
| CN | 101437663 B | 6/2013 |
| CN | 104513354 A | 4/2015 |
| CN | 105602181 A | 5/2016 |
| JP | 2004147573 A | 6/2005 |
| JP | 2005147573 A | 6/2005 |
| JP | 2005327965 A | 11/2005 |
| JP | 2015041419 A | 3/2015 |
| KR | 100959883 B1 | 5/2010 |
| WO | 2012015472 A1 | 2/2012 |
| WO | 2016114389 A1 | 7/2016 |

OTHER PUBLICATIONS

Miartinez-Rubi et al., Nanotube-Buckypaper/Polyurethane composites with enghanced mechanical properties, Jul. 19-24, 2015, pp. 1-7, Copenhagen, Denmark.
Weisshaar, Terrence A., Morphing Aircraft Systems: Historical Perspectives and Future Challenges, Aerospace Research Central, vol. 50, No. 2, Mar. 2013, United States.
Ashrafi, Behnam, et al. Highly Stretchable Strain Sensor based on Polyurethane-Impregnated Carbon Nanotube Buckypaper. 2016.
Ashrafi, Behnam et al. Electrically Responsible Polyurethane-CNT Sheets for Sensing and Heating. Canadian inetnational Conference on Composite Materials, 2017.
Ashrafi, Behnam, Martinez-Rubi, Yadienka, Jakubinek, Michael B., et al. Multifunctional Polyurethane-enhanced Buckypaper Sheets based on Carbon Nanotubes and Boron Nitride Nanotubes. 21st International Conference on Composite Materials, 2017.
Brandon, Erik J., Vozoff, Max, Kolawa, Elizabeth A., et al. Structural health management technologies for inflatable/deployable structures: Integrating sensing and self-healing. Acta Astronautica, 2011, vol. 68, No. 7-8, p. 883-903.
Bubert, Edward A., Woods, Benjamin KS, Lee, Keejoo, et al. Design and fabrication of a passive 1D morphing aircraft skin. Journal of intelligent material systems and structures, 2010, vol. 21, No. 17, p. 1699-1717.
Cadogan, David, Stein, J., et Grahne, Mark. Inflatable composite habitat structures for lunar and mars exploration. Acta Astronautica, 1999, vol. 44, No. 7 12, p. 399-406.
Cho, Jae Whan, Kim, Jeong Won, Jung, Yong Chae, et al. Electroactive shape-memory polyurethane composites incorporating carbon nanotubes. Macromolecular Rapid Communications, 2005, vol. 26, No. 5, p. 412-416.
Hinkle, Jonathan, Lin, John, et Kling, Daniel. Design and materials study on secondary structures in deployable planetary and space habitats. In : 52nd AIAA/ASME/ASCE/AHS/ASC Structures, Structural Dynamics and Materials Conference 19th AIAA/ASME/AHS Adaptive Structures Conference 13t. 2011. p. 2024.
Hinkle, Jonathan, Cadogan, David, Roushey, Jeff, et al. Design and testing of resilient expandable structure using multi-layer softgoods technology. In : 53rd AIAA/ASME/ASCE/AHS/ASC Structures, Structural Dynamics and Materials Conference 20th AIAA/ASME/AHS Adaptive Structures Conference 14th AIAA. 2012. p. 1514.
Ivanco, Thomas, Scott, Robert, Love, Michael, et al. Validation of the Lockheed Martin morphing concept with wind tunnel testing. In : 48th AIAA/ASME/ASCE/AHS/ASC Structures, Structural Dynamics, and Materials Conference. 2007. p. 2235.
Jakubinek, M.B. et al. Large-scale production of boron nitride nanotubes, developement of nonwoven sheets, and applications for textile composites. TEXCOMP-12 Conference, May 26-29, 2015, Raleigh, NC, USA, 2015.
Jakubinek, Michael, Ashrafi, Behnam, Martinez-Rubi, Yadienka, et al. Multifunctional skin materials based on tailorable, carbon-nanotube-polyurethane composite sheets. In : 2018 AIAA/ASCE/AHS/ASC Structures, Structural Dynamics, and Materials Conference. 2018. p. 1154.
Jakubinek, Michael, Roy, Steven, Palardy-Sim, Marc, et al. Stretchable structure for a benchtop-scale morphed leading edge demonstration. In : AIAA Scitech 2019 forum. 2019. p. 1857.
Kikuta, Michael Thomas. Mechanical properties of candidate materials for morphing wings. 2003. These de doctoral. Virginia Tech.
Kim, Keun Su, Jakubinek, Michael B., Martinez-Rubi, Yadienka, et al. Polymer nanocomposites from free-standing, macroscopic boron nitride nanotube assemblies. RSC Advances, 2015, vol. 5, No. 51, p. 41186-41192.
Martinez-Rubi, Y., Ashrafi, B., Jakubinek, M., et al. Integration of Nanotube Paper into UHMWPE Multilayer Structures. In : Design, Manufacturing and Applications of Composites Tenth Workshop 2014: Proceedings of the Tenth Joint Canada-Japan Workshop on Composites, Aug. 2014, Vancouver, Canada. DEStech Publications, Inc, 2015. p. 62.
Martinez-Rubi, Y., Ashrafi, B., Jakubinek, M., et al. Production of polyurethane nanotube composites with tailorable properties and fuctionalities. Canadian International Conference on Composite Materials, 2017.
Martinez-Rubi, Y., Ashrafi, B., Jakubinek, M., et al. PNanotube-buckypaper polyurethane composites with enhanced mechanical properties and integration into hybrid structures. Canadian International Conference on Composite Materials, 2015.
McKnight, Geoffrey, Doty, Robert, Keefe, Andrew, et al. Segmented reinforcement variable stiffness materials for reconfigurable surfaces. Journal of Intelligent Material Systems and Structures, 2010, vol. 21, No. 17, p. 1783-1793.
Olympio, Kingnide Raymond, Gandhi, Farhan, Asheghian, Laila, et al. Design of a flexible skin for a shear morphing wing. Journal of intelligent material systems and structures, 2010, vol. 21, No. 17, p. 1755-1770.

(56) References Cited

OTHER PUBLICATIONS

Schorsch, Oliver, Luhring, A., Nagel, Christof, et al. Polymer based morphing skin for adaptive wings. In : 7th ECCOMAS thematic conference on smart structures and materials Smart. 2015.
Thill, C. L., Etches, J., Bond, I., et al. Morphing skins. The aeronautical journal, 2008, vol. 112, No. 1129, p. 117-139.
First Office Action in corresponding application in China No. 201880032585.1, dated Jul. 2, 2021.
Wakasugi, Takashi, the solubilities of BN in B2O3 bearing melts, Journal of Non-Crystalline Solids 135, 1991, 139-135, North-Holland.

\* cited by examiner

STRETCHABLE NANOCOMPOSITE SKIN MATERIAL AND RELATED STRUCTURES

TECHNICAL FIELD

The technical field generally relates to nanocomposite materials and more particularly to a stretchable nanocomposite skin material and related structures thereof.

BACKGROUND

Nanocomposite materials are good candidates to be used as deformable materials, while offering desirable mechanical resistance properties. Typically, nanotubes are dispersed in polymer or nanotube sheets are subsequently infused with polymer resin to produce a deformable nanocomposite, such as a bendable or stretchable nanocomposite.

Regarding advances in the domain of nanocomposites, US patent application published under No. 2015/147573 provides examples (see examples 32 and 90) showing methods for fabrication of elastomerically deformable carbon nanotube sheets, including deposition of a nanofiber sheet on an elongated elastomeric sheet (porous elastomeric textile or porous silicon rubber sheet), such that the resulting deformable sheet can be elastically relaxed and re-stretched repeatedly to the initial elongation without undergoing a substantial resistance change. Methods may further include overcoating with a second elastomeric sheet. The principle of the method may also be extended to produce elastomerically deformable stacks comprising one or more nanotube electrode sheets that are laminated between sheets of elastomer.

Another example of a deformable nanocomposite material is provided by Martinez-Rubi Y et al. *Nanotube-Buckypaper/Polyurethane Composites with Enhanced Mechanical Properties*. 20th International Conference on Composite Materials, Copenhagen, 19-24 Jul. 2015 (Referred hereinafter as Martinez-Rubi). Martinez-Rubi discloses a non-woven sheet of a carbon nanotube/thermoplastic polyurethane composite (CNT/TPU). The CNT/TPU composite sheet can be used as an interlayer between sheets of ultra-high molecular weight polyethylene (UHMWPE).

A further example of a deformable nanocomposite material is provided by Koerner H, et al. *Deformation-morphology correlations in electrically conductive carbon nanotube-thermoplastic polyurethane nanocomposites*. Polymer. 46 (2005) 4405-4420. Koerner discloses a single layer CNT/TPU composite sheet or film which is stretchable.

Morphing and deployable structures require a deformable skin to enable shape change while maintaining a continuous outer surface over a support structure. In existing implementations, the skin can be reshaped with minimal area change (e.g., bending), but there is a need for a skin which is able to stretch by incorporating changes in area. Existing stretchable materials include elastomeric polymers such as silicones, rubber, thermoplastic polymers, shape memory polymers, and nonwovens. Each of these available materials may be a candidate to be used as skin material, but has disadvantages including insufficient stiffness for aerodynamic load, permeability, timescale of the transition, etc.

Conceiving a material that can stretch to a sufficient extent, stretch reversibly where required, and also offer required stiffness to support loads is a challenge for the development of improved morphing and deployable structure technologies.

SUMMARY

In a first aspect, there is provided a stretchable multiple-layer nanocomposite material comprising at least a nanocomposite material layer comprising a network of nanotubes modified with an elastomeric polymer; and at least one additional layer laminated with the nanocomposite material layer.

In some implementations, the network of nanotubes is provided by a non-woven sheet of nanotubes. The nanotubes may be oriented, either randomly or in controlled alignment, within a plane defined by the nanocomposite material layer.

In some implementations, the nanotubes comprise carbon nanotubes, boron-nitride nanotubes, boron-carbon-nitrogen nanotubes, silicon-carbide nanotubes, other nanoparticles, hybrids thereof or a combination thereof. The nanotubes include single-walled nanotubes and multi-walled nanotubes. The nanocomposite material layer may have a nanotube content between 5 wt % and 90 wt %, optionally between 10 wt % and 40 wt %.

In some implementations, the elastomeric polymer comprises thermoplastic elastomers, thermoplastic polyurethane, rubber, silicone rubber or a combination thereof.

Each of the previously mentioned layers may be combined in various combinations and the material may include several layers of the same type.

In some implementations, the nanocomposite material layer is a first nanocomposite material layer and the at least one additional layer is another nanocomposite material layer comprising nanotubes differing in nature from the nanotubes of the first nanocomposite material layer. Optionally, the nanocomposite material layer is a first nanocomposite material layer and the at least one additional layer may be another nanocomposite material layer having a nanotube content which is different from the first nanocomposite material layer. Alternatively, the nanocomposite material layer is a first nanocomposite material layer and the at least one additional layer may be another nanocomposite material layer similar to the first nanocomposite material layer.

Furthermore, the at least one additional layer may be a neat polymer layer, a composite polymer layer, or a reinforced polymer layer including at least one elastomeric polymer. The elastomeric polymer of the at least one additional layer may be the same as the one included in the nanocomposite material layer. Alternatively, the elastomeric polymer of the at least one additional layer may be different from the one included in the nanocomposite material layer.

In some implementations, the multiple-layer material may have mechanical properties varying across a surface area thereof. At least the nanocomposite material layer may have mechanical properties varying across a surface area thereof.

For example, the multiple-layer material may have a nanotube content varying across the surface area. The nanotube content may be higher in a specific area of the nanocomposite layer to enhance stiffness of the material. In another example, the material may have a polymer content varying across the surface area. The polymer content may be higher in another specific area of the multiple-layer nanocomposite material to enhance stretchability of the material. In yet another example, the nature of elastomeric polymer and/or the nature of the nanotubes may change across the surface area of the multiple-layer material.

In some implementations, the multiple-layer material comprises a plurality of layers which number varies across the surface area of the material. The number of layers may be tailored to obtain a given material thickness and properties profile adapted for use as a skin material.

In further implementations, the multiple-layer material has a nanotube:polymer ratio tailored to provide a given stretchability profile to the skin material for application in a morphing structure or a deployable structure.

In another aspect, there is provided a skin material for direct application as a skin on a substructure, the skin material comprising a nanotube network modified with a polymer. The polymer may comprise an elastomeric polymer selected to provide stretchability to the skin material.

In some implementations, the skin material includes a non-woven nanotube layer modified with the polymer. In addition, at least one additional layer may be laminated on the non-woven nanotube layer modified with the polymer.

Optionally, the at least one additional layer is one or more of a nanocomposite layer. Further optionally, the at least one additional layer is a layer of neat or reinforced elastomeric polymer comprising thermoplastic polyurethane, silicone rubber, rubber or a combination thereof.

In some implementations, the skin material includes a plurality of laminated layers tailored to obtain a material thickness between 0.05 mm and 20 mm. Optionally, the material thickness is between 0.5 mm and 3 mm.

In some implementations, the skin material has a composition tailored to provide a reversible stretch capacity from 5 to 50% and an elastic modulus from 50 MPa to 10 GPa. Optionally, the reversible stretch capacity is of 20% and the elastic modulus is of 500 MPa.

In some implementations, the skin material has a nanotube:polymer ratio tailored to provide a one-time stretch capacity of at least 100% and a stiffness from 50 MPa to 10 GPa. Optionally, the one-time stretch capacity is of at least 200% stretch and the stiffness of 500 MPa.

In another aspect, there is provided a stretchable skin material being the stretchable multiple-layer nanocomposite material defined above.

In another aspect, there is provided a skin being directly applied onto a support surface as the stretchable multiple-layer nanocomposite material or skin material defined above. In some implementations, the nature of the nanotubes included in the material are selected to provide heating, sensing, EMI shielding, neutron shielding properties or a combination thereof to the skin.

In another aspect, there is provided a morphing structure produced by direct application of a skin material as defined above onto a support structure. The morphing structure may be at least a portion of a morphing aircraft, comprising a wing leading edge, a wing trailing edge, a tail fin, a nose cone or a combination thereof.

In another aspect, there is provided a deployable structure produced by direct application of a skin material as defined above onto a deployable support structure. The deployable support structure may reversibly unfold and/or inflate resulting in stretching of the skin material. Optionally, the skin material is maintained in a stretched state by internal air pressure when the support structure is deployed, the internal air pressure being higher than a pressure external to the deployable structure. The deployable structure may be at least a portion of a deployable space habitat or a deployable military habitat.

In another aspect, there is provided a structure including a sub-structure and a skin as defined above to form at least part of an outer surface of the structure by application onto the sub-structure.

While the skin material will be described in conjunction with exemplary implementations, it will be understood that it is not intended to limit the scope of the material to such implementations. On the contrary, it is intended to cover all alternatives, modifications and equivalents as may be included as defined by the present description. The objects, advantages and other features of the skin material and related applications will become more apparent and be better understood upon reading of the following non-restrictive description, given with reference to the accompanying drawings.

BRIEF DESCRIPTION OF THE DRAWINGS

Implementations of the stretchable multiple-layer nanocomposite material for a skin material, a skin, a morphing structure or a deployable structure are represented in and will be further understood in connection with the following figures.

Figure 1:
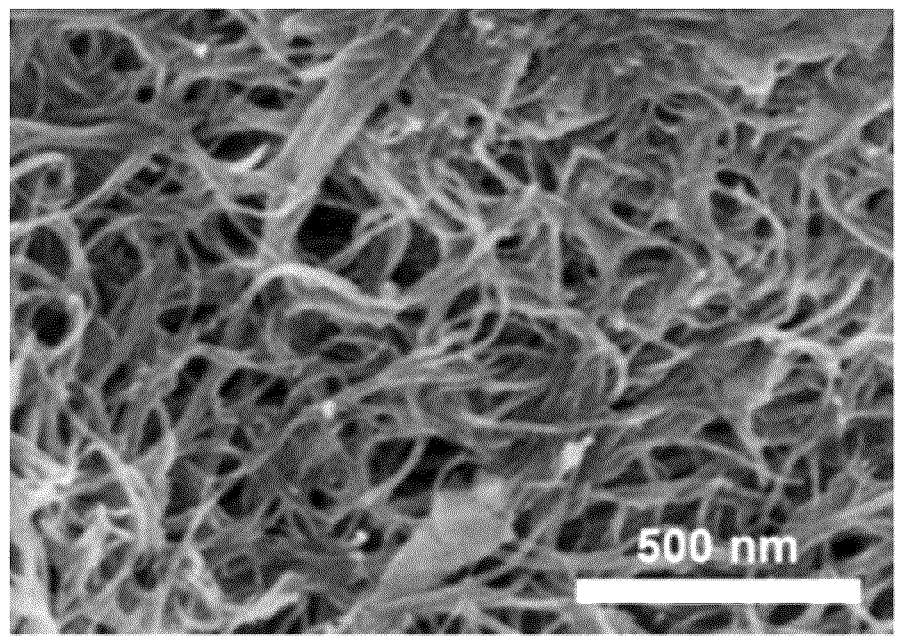
FIG. 1 is an SEM image of a non-woven nanocomposite sheet (also referred to as buckypaper composite) using multi-walled carbon nanotubes modified with thermoplastic polyurethane (CNT-TPU, also referred to as NT-PU).

While the invention will be described in conjunction with example embodiments, it will be understood that it is not intended to limit the scope of the invention to these embodiments. On the contrary, it is intended to cover all alternatives, modifications and equivalents as may be included as defined by the appended claims.

DETAILED DESCRIPTION

Lamination of non-woven sheets of nanotubes modified with an elastomeric polymer produces a tailorable, stretchable skin material. Details regarding implementations of the stretchable skin material, manufacture thereof, resulting skin and skin applications in morphing and deployable structures are provided hereinafter.

It should be noted that the same numerical references or annotations refer to similar elements. Furthermore, for the sake of simplicity and clarity, namely so as to not unduly burden the figures with several references, not all figures contain references to all the components and features, and references to some components and features may be found in only one figure, and components and features of the present disclosure which are illustrated in other figures can be easily inferred therefrom. The embodiments, geometrical configurations, materials mentioned and/or dimensions shown in the figures are optional, and are given for exemplification purposes only. Therefore, the descriptions, examples, methods and materials presented in the claims and the specification are not to be construed as limiting but rather as illustrative only.

Moreover, although the embodiments of the skin material and corresponding compositions and structures thereof consist of certain geometrical configurations as explained and illustrated herein, not all of these components and geometries are essential and thus should not be taken in their restrictive sense. It is to be understood, as also apparent to a person skilled in the art, that other suitable components and cooperation thereinbetween, as well as other suitable configurations, may be used for the skin material as will be briefly explained herein and as can be easily inferred herefrom by a person skilled in the art.

In the present description, an embodiment is an example or implementation of the inventions. The various appearances of "one embodiment," "an embodiment", "some embodiments", or "some implementations" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment.

It is further to be understood that where the claims or specification refer to "a" or "an" element, such reference is not be construed that there is only one of that element. It is to be understood that where the specification states that a component, feature, structure, or characteristic "may", "might", "can" or "could" be included, that particular component, feature, structure, or characteristic is not required to be included.

Single-Layer Nanocomposite Material Implementations

In a first implementation, there is provided a stretchable nanocomposite material including a non-woven sheet of carbon nanotubes defining a network of nanotubes which are combined with an elastomeric polymer, as a single layer. Combination of the nanotube network and polymer produces a polymer modified nanotube network. It should be noted that combination of the elastomeric polymer with the nanotubes refers to the association of the polymer with the nanotube surface or incorporation of the polymer within the nanotube network.

The nanotubes include carbon nanotubes (CNTs), boron nitride nanotubes (BNNTs), boron carbon nitrogen nanotubes (BCNNTs), silicon carbide nanotubes (SiCNTs), other nanoparticles, and hybrids or combinations thereof. The nanotubes include single-wall nanotubes and multi-wall nanotubes. The nanotubes may be substantially pure, doped, functionalized or a combination thereof.

It should be understood herein that nature of the nanotubes includes type (CNT, BNNT, BCNNT, SiCNT), dimension, structure (single-wall, multi-wall), state (doped/functionalized/pure).

The elastomeric polymer may include thermoplastic elastomers (such as thermoplastic polyurethanes), silicones, rubbers and combinations thereof. It should be noted that stiffness is herein defined as a resistance to deformation by stretching or bending.

Stretchability is further defined herein as a capacity to elongate under a stress imposed in a primary direction (axial load). The elongation may be permanent and further described as one-time stretching or maximal stretching. The elongation may be reversible and further described as reversible stretching. Stretchability is to be distinguished from bendability, the latter referring to a capacity to bend, i.e. to deform (with minimal area change and no substantial elongation) when an external load is applied perpendicularly to the primary direction.

It should be understood that the content of nanotubes and elastomeric polymer may vary to meet selected mechanical strength criteria without departing from the scope of the present invention. For example, the nanotube content of the material may be increased to enhance stiffness of the material, and the elastomeric polymer content may be increased to enhance stretchability of the material. Consequently, manufacture of the stretchable nanocomposite material sheet may include controlling a nanotube:polymer ratio according to a mechanical strength criteria of the nanocomposite material sheet. Optionally, the material has a nanotube content ranges between 5 wt % and 90 wt %, an elastomeric polymer content between 10 wt % and 95 wt %, so as to reach a stiffness between 0.1 and 10 GPa and a stretchability between 10 and 1000%. The resulting sheet is thin and porous, i.e. having a thickness between 0.005 mm and 1 mm, optionally between 0.05 mm and 0.15 mm, and a porosity between 10 and 90 vol %.

In another implementation, the single-layer nanocomposite material may be manufactured as a single-layer non-woven sheet of nanotubes modified with an elastomeric polymer according to several methods. For example, in a first step, an elastomeric polymer component is dissolved within a suitable solvent (e.g. acetone, THF, choloroform). Separately, the nanotubes are dispersed (e.g. sonically) in a polymer non-solvent (e.g. alcohol). The components are then combined to form a homogeneous suspension. Control of the solvent system and nanotube concentration is employed to fabricate sheets of tailorable composition and properties, following filtration of the suspension, where the polymer is associated with the nanotube surface and the nanotube:polymer ratio can be tailored to adjust the properties from more extensible to more stiff. The material output of that method is a thin, porous, non-woven sheet of polyurethane-modified nanotubes with a controllable, high nanotube content by weight.

FIG. 1 is an SEM image of a single-layer NT-TPU composite manufactured according to the above-described method. Martinez-Rubi et al., Nanotube-buckypaper/polyurethane composites with enhanced mechanical properties, $20^{th}$ ICCM, Copenhagen, 19-24 Jul. 2015, and Ashrafi et al., Highly stretchable strain sensor based on Polyurethane-Impregnated Carbon Nanotube Buckypaper, ProcASC, 2016, are herein incorporated by reference.

Figure 6:
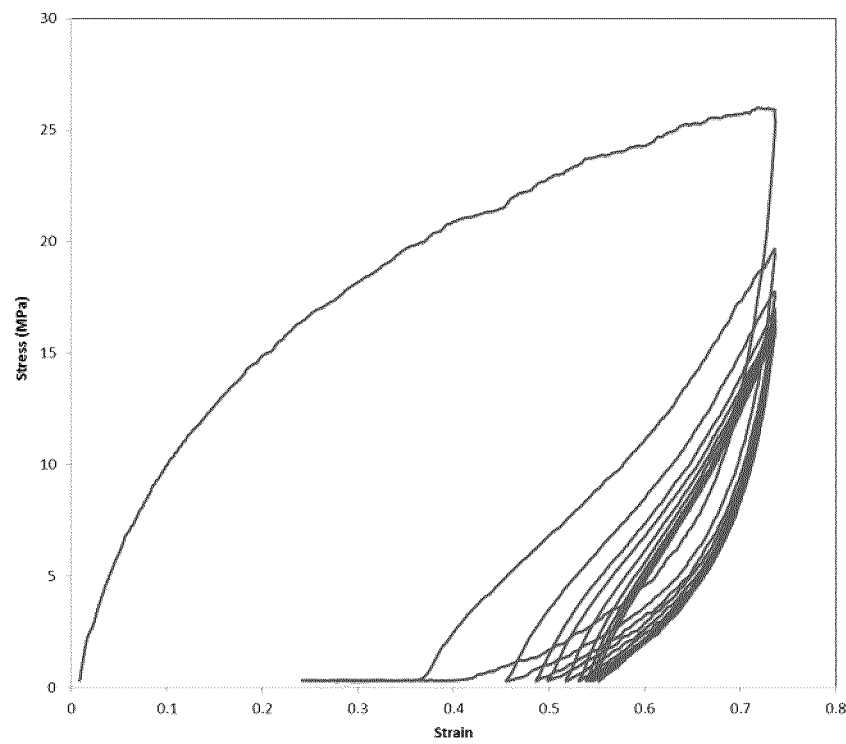
FIG. 6 is a graph of a load versus displacement under stretching load showing initial pre-stretch and subsequent cycling for a stretchable single-layer polyurethane-nanotube composite material.

In some implementations, the resulting single-layer nanocomposite material is then pre-stretched. FIG. 6 shows an example of pre-stressing and strain stress cycling of a nanotube-polyurethane composite to achieve stable cycling for a stretchable material.

Multi-Layer Nanocomposite Material Implementations

In another implementation, there is provided a stretchable multi-layer nanocomposite material including at least one stretchable non-woven nanocomposite material sheet. As defined above, the stretchable non-woven nanocomposite material sheet includes a network of nanotubes which are modified with an elastomeric polymer, as a single layer. At least one additional layer is laminated on the stretchable non-woven nanocomposite material sheet. The at least one additional layer may be another stretchable non-woven nanocomposite material sheet, a sheet of neat elastomeric polymer, or a sheet of reinforced elastomer.

Figure 7A:
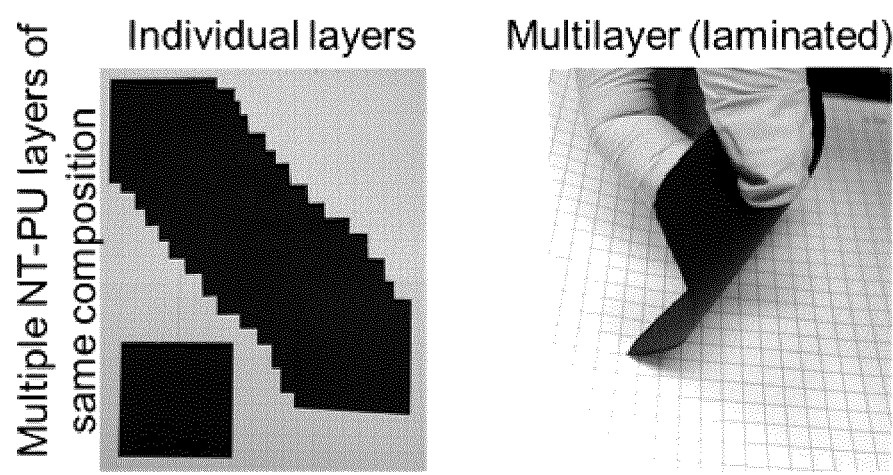
FIG. 7A includes two photographs showing respectively multiple individual layers of CNT-TPU, and a multilayer skin material resulting from lamination of the multiple individual layers of CNT-TPU.

Advantageously, layering enables to reach a given material thicknesses while keeping the nanotube orientation primarily in the plane of the material. It should be noted that the nanotubes are randomly aligned within the plane of the single-layer sheet, and this alignment is maintained during superposition of a plurality of single-layer sheets, while achieving a targeted thickness. In the exemplary implementation illustrated in FIG. 7A, a multiple-layer nanocomposite material sheet is produced from a stack of superposed multiple single-layer sheets of the same material by lamination.

In some implementations, the manufacture of the material may include controlling the number of layers in accordance with a targeted thickness for the multiple-layer nanocomposite material.

Experimentation shows that lamination of multiple single-layer non-woven nanocomposite material sheets enables to increase a thickness of the material while substantially keeping or even improving the stretchability provided by a single-layer sheet of the same material. Additional properties may therefore be conferred by lamination such as enhanced mechanical resistance, enhanced stretchability and impermeability of the resulting multi-layer material.

It should be noted that the additional layers which are laminated on the single-layer non-woven nanocomposite sheet may therefore be made of any available material able to stretch and/or offering suitable mechanical resistance. Lamination offers multiple possibilities of layer combinations to obtain tailored mechano-chemical properties for the resulting material. Results of the lamination in terms of mechanical properties depend on whether the laminated sheets are identical or different in composition, as well as on pressure and temperature. The resulting multi-layer material is thicker and densified that can retain a similar or enhanced range of properties to the initial non-laminated sheets.

Lamination techniques include hot pressing, vacuum bagging and autoclave. For example, single-layer polyurethane-modified nanotube sheets are first layered to form a stack of single-layer sheets and then laminated in a hot press to form a thicker, densified multiple-layer nanotube-polyurethane composite sheet.

Figure 2A:
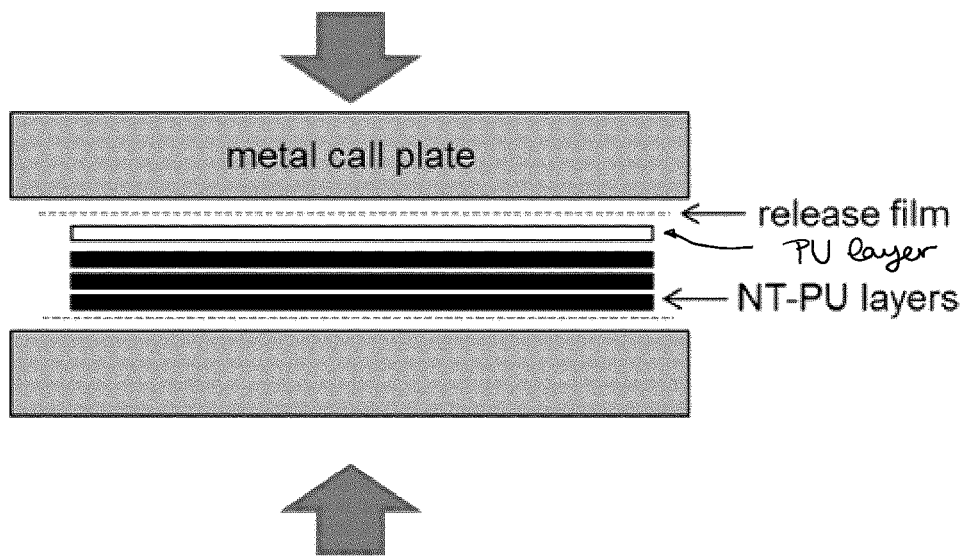
FIGS. 2A and 2B are schematic representation of the lamination process for two respective combinations of layers of the nanocomposite material.
Figure 2B:
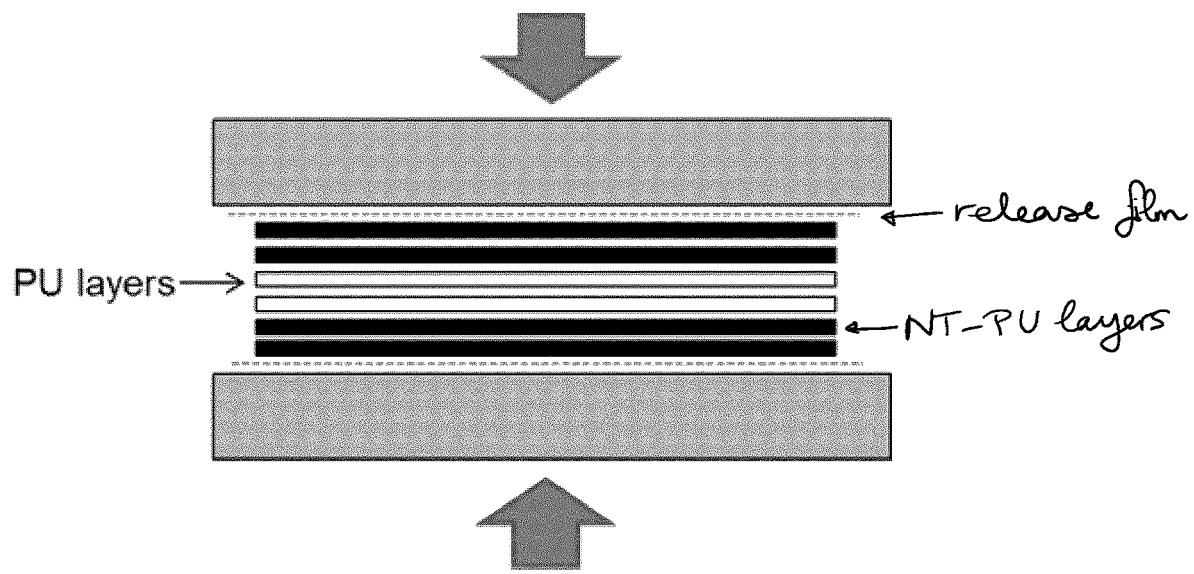
Figure 7B:
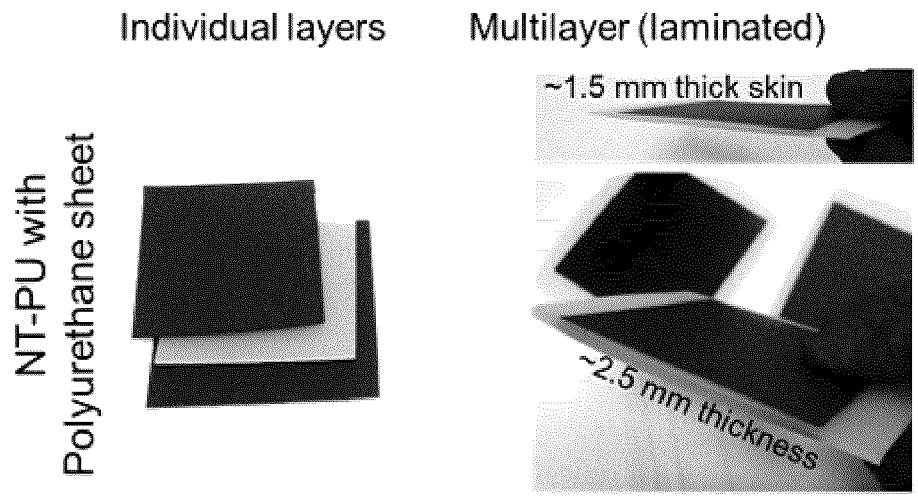
FIG. 7B includes two photographs showing respectively two upper and lower layers of CNT-TPU and an intermediate layer of TPU, and a multilayer skin material resulting from lamination of the three layers.

FIGS. 2A and 2B offer schematic representation of lamination of multiple polyurethane-modified nanotube material layers (referred to as NT-PU layers in these Figures or CNT-TPU within the description) and at least one neat polyurethane (PU) layer. The at least one additional polyurethane layer may be laminated as a surface layer as seen on FIG. 2A or as an intermediate layer in a sandwich-like structure as seen on FIG. 2B. Optionally, a release film as seen on FIGS. 2A and 2B may be used on the external surface of the exposed layers of the material to facilitate release of the material subsequently to the hot pressing step. The sandwich-like combination from FIG. 2B includes stiffer layers near the top and bottom and thereby provides high bending stiffness while using less of the stiff material and improving the reversible stretch capacity. FIG. 7B provides a photograph of such resulting sandwich-like combination as skin material. The structure of this material provides for an increased resistance to bending loads (i.e., higher modulus of elasticity in bending than the polymer) while minimizing the increase in actuation force (i.e., minimizing increase in the elastic modulus in tension).

The approach of layering also provides for additional control by varying the composition of the multiple-layer nanocomposite material sheet vertically from layer-to-layer, or across the surface area of the sheet.

In some implementations, the additional stretchable non-woven nanocomposite material layer may differ from the first stretchable non-woven nanocomposite material layer in various ways. For example, the type of nanotubes may be varied such that the multi-layer nanocomposite material includes a first non-woven single-layer sheet of CNTs modified with thermoplastic polyurethane and a second non-woven single-layer sheet of BNNTs modified with thermoplastic polyurethane. Further optionally, the type of elastomeric polymer may be varied such that the multi-layer nanocomposite material sheet includes a first non-woven single-layer sheet of CNTs modified with thermoplastic polyurethane and a second non-woven single-layer sheet of CNTs modified with silicone rubber. As it may be appreciated, one skilled in the art would understand that various combinations of layers may be performed according the type and number of available nanotubes and polymer combinations.

Vertical variation of the mechanical properties may be performed for example by stacking, before lamination, single-layer nanocomposite material sheets having different compositions (nanotube nature and content, polymer nature and content). Additionally, nanotubes from a first layer may be oriented in one direction whereas the nanotubes from an adjacent layer may be oriented in another direction (within the plane of the sheet) to influence anisotropic properties.

In other implementations, the multi-layer material may have varying mechanical and physico-chemical properties along a surface area of the material. For example, higher stretch under uniform load (or higher stiffness) may be provided in certain areas of the multi-layer material by decreasing (or increasing) the ratio of nanotube:polymer and increasing (or decreasing) the number of neat elastomeric polymer layers in these areas.

Variation of the mechanical properties across the surface area of the multiple-layer sheet may be obtained by joining side-by-side two or more multiple-layer or single-layer nanocomposite material sheets. For example, two single-layer nanocomposite material sheets having different composition may be joined side-by-side to obtain another larger single-layer material sheet having varying mechanical properties across a surface area thereof. Lamination of one or more additional layers is performed on the larger single-layer material sheet to produce the final multiple-layer nanocomposite material sheet having mechanical properties varying across the surface area of the sheet. Another way to obtain variation of the properties across the surface area may include producing two multiple-layer nanocomposite material sheets having two different sets of mechanical properties and joining them side-by-side through hot pressing to produce a larger multiple-layer material sheet having mechanical properties varying across the surface area of the sheet.

Skin Material Implementations

The stretchable multi-layer nanocomposite material produced by lamination can be directly used as skin material to form a stretchable skin.

It should be noted that skin material refers herein to a continuous multiple-layer material that is applied to a sub-structure so as to form an outer surface of a structure. A compliant skin refers herein to a skin able to react in compliance with the shape of the sub-structure and the tensile load applied thereon.

A compliant skin includes bendable skins and stretchable skins. Skin material performance is tailored according to various criteria including the ratio of nanotubes to elastomeric polymer, the type of nanotubes, the functionalization of the nanotubes, the lamination pattern of the multiple-layer material and the composition of each layer. Stretchable skin material may be advantageously used as a morphing or deployable skin.

In some implementations, the combined stretchability (offered by the elastomeric polymer) and stiffness (offered by the nanotubes) of the multi-layer nanocomposite material enables to produce a suitable morphing skin that can change shape according to the sub-structure modifications and/or load applied thereon, while maintaining sufficient stiffness for keeping integrity of the outer surface and associated mechano-chemical properties.

To ensure adequate mechanical resistance and stretchability, the at least one layer of nanocomposite material forming the skin material may be characterized by a nanotube content between 10 wt % and 90 wt %, optionally between 10 and 45 wt %, further optionally between 20 and 40 wt %. Lamination may be performed to obtain a skin material with a thickness between 0.05 mm and 20 mm, optionally between 0.5 mm and 1.5 mm, further optionally between 0.5 mm and 3 mm, while keeping the morphing ability.

Morphing or Deployable Structure Implementations

The multi-layer nanocomposite material is used as a skin material to form a morphing or deployable structure. The skin material is directly applied as a stretchable skin on an underlying sub-structure, providing a continuous aerodynamic surface and supporting loads across the underlying sub-structure while enabling significant stretch (area change).

It should be noted that direct application of the skin material as a skin refers to the ability of using the skin material defined herein as a skin without the need to combine the skin material with additional reinforcing means, layer or material. It should also be noted that the skin material is attached to the surface of the sub-structure by means available to one skilled in the art according to the application and material surface of the sub-structure. It should further be noted that choice of the sub-structure design and material is to be chosen is accordance with the skin material to be used as a skin.

It should further be noted that the skin material may be continuously supported by the sub-structure in certain areas and discontinuously supported in other areas of the resulting structure.

Figure 9A:
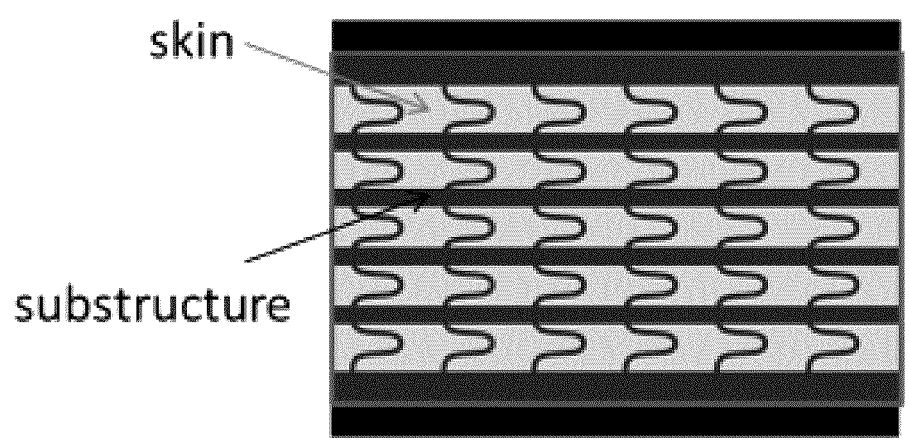
FIG. 9A is a schematic representation of a stretchable morphing structure including a skin formed with the skin material applied on a sub-structure.
Figure 9B:
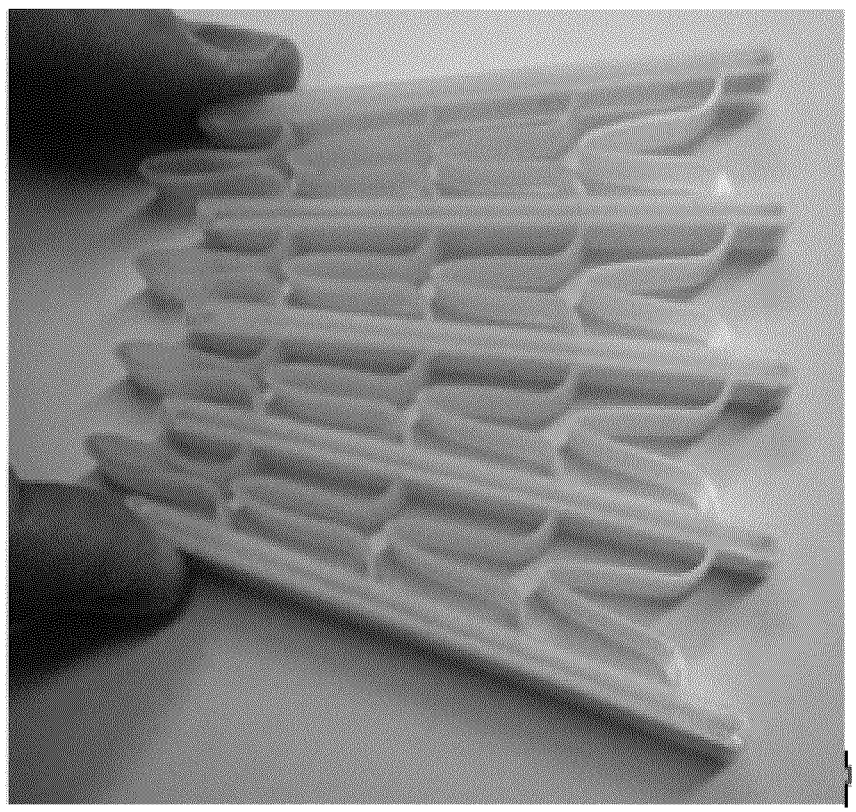
FIG. 9B is a photograph of a sub-structure according to FIG. 9A produced by 3D printing.

For example, the skin may be applied to a substructure (see FIG. 9B) to form a stretchable morphing structure (see FIG. 9A).

In some implementations, the method of manufacture of the stretchable skin, based on the multi-layer nanocomposite material described herein, includes tailoring the mechanical resistance properties and stretchability to the outer surface of the underlying sub-structure to which the skin is attached. For example, the sub-structure may include an unfolding area and the stretchable skin may be manufactured such that a portion thereof is capable of higher stretching when the corresponding area of the sub-structure is unfolded.

The morphing structures encompassed herein include morphing wings in aeronautic domain. The deployable structures encompassed herein include deployable habitats such as deployable military habitats and deployable space habitats.

In some implementations, the skin material defined herein may be used as part of a morphing wing to form a morphing leading edge in place of slats in a high-lift system. The multi-layer nanocomposite material is used as skin material to form the morphing leading edge of the wing, thereby increasing the wing area by changing shape while maintaining a continuous surface due to the stretch of the skin material. Presence of the nanotube network offers required stiffness to support aerodynamic loads and minimize secondary support-structure weight.

It should be understood that the laminated non-woven sheets of nanotubes modified with elastomeric polymer may be used as a skin material on any parts of a wing or plane, including wing trailing edge, tail fin or nose cone, to offer a morphing continuous surface and improve aerodynamic efficiency for any take-off, landing and cruise conditions, and to improve maneuverability of the aircraft.

In other implementations, the skin material may be used as at least a portion of the outer surface of a deployable structure and the material may be maintained in a stretched state by internal air pressure when the support structure is deployed, the internal air pressure being higher than a pressure external to the deployable structure.

An example of tailoring mechanical properties over the area of the multilayer assembly (or skin) would be to have higher loadbearing ability in some areas (e.g., right at the front of the leading edge or in an impact-prone location) and hence accepting less stretch in those areas. The location where the stretchable skin is bonded to the rest of the structure can also be subject to stress concentration and hence modulating the mechanical properties approaching that location may be beneficial.

For example, one or more lower stiffness surface or internal layers, are relevant for surface finish and optimizing properties, respectively. Adding a surface layer of different nanotube content, neat elastomer, or a different elastomer composition could be beneficial for wear, paintability or bonding between the skin and structure.

It should be noted that maximal reversible stretch capacity may be favored when developing a stretchable skin for morphing structures, whereas maximal one-time stretch may be favored when developing skin for deployable structures. In addition, differences in impact resistance may be tailored to the shape of the plane or habitat.

Multifunctional Material Implementations

Advantageously, the nanotube network may be selected and optimized to meet the requirements of a stretchable skin material while simultaneously performing one or more functions including heating, sensing, EMI shielding, neutron shielding and combinations thereof. A multifunctional skin material and resulting multifunctional morphing or deployable structures are thereby provided.

In some implementations, carbon nanotubes (CNTs) are selected to provide an electrical network within the skin material and thereby impart at least one of a heating function or a sensing function to the skin material.

For example, the heating skin material may be applied to a wing such that the outer surface of the wing is able to be heated to control the temperature-dependent mechanical properties and/or make the skin de-iceable in flight by heating to allow morphing thereof.

In another example, the sensing skin material may be applied to a deployable structure and thereby provides health-monitoring of the outer surface to detect damage to the skin resulting from cycling or impacts.

In yet another example, the conductive skin material may be applied to form an enclosure and provides EMI shielding to the inside of the enclosure.

In other implementations, BNNTs may be used in place of or in addition to CNTs to provide thermal properties to the skin material. The BNNTs network of the composite material thereby provides neutron radiation shielding to a deployable space structure.

It should be understood that any one of the above-mentioned aspects of each nanocomposite sheet, multi-layer nanocomposite material, skin material, morphing and deployable structures, and manufacture method related thereto may be combined with any other of the aspects thereof, unless two aspects clearly cannot be combined due to their mutually exclusivity. For example, the various manufacture steps and/or structural elements of the non-woven nanocomposite material sheet described hereinabove, herein-below and/or in the appended Figures, may be combined with any of the general manufacture method or features of the multifunctional morphing structure descriptions appearing herein and/or in accordance with the appended claims.

EXPERIMENTAL RESULTS

Experiments have been performed to evaluate the mechanical properties of several samples of polyurethane-modified CNT non-woven sheets, and of single sheets versus multilayer laminated material.

In this section, the term "about" means within an acceptable error range for the particular value as determined by one of ordinary skill in the art, which will depend in part on how the value is measured or determined, i.e. the limitations of the measurement system. It is commonly accepted that a 10% precision measure is acceptable and encompasses the term "about". The symbol "~" is to be understood as "about".

UAF™ 472 refers to a polyurethane adhesive tape based on thermoplastic ester, and Tecoflex™ 80A and 100A are polyether based aliphatic thermoplastic polyurethanes.

TABLE 1

Comparison of tensile properties of several polyurethane-modified CNT sheets using industrial grade MWCNTs to the neat polyurethanes.

| Material | Modulus (MPa) | Strength (MPa) | Failure Strain |
|---|---|---|---|
| UAF 472 (0% CNT) | ~100 | ~6 | >500%* |
| UAF 472 - 20% CNT | ~350 | ~28 | ~200% |
| UAF 472 - 30% CNT | ~2300 | ~34 | ~80% |

TABLE 1-continued

Comparison of tensile properties of several polyurethane-modified CNT sheets using industrial grade MWCNTs to the neat polyurethanes.

| Material | Modulus (MPa) | Strength (MPa) | Failure Strain |
|---|---|---|---|
| Tecoflex 80A (0% CNT) | ~7 | ~2.5 | 660%*,** |
| Tecoflex 80A-25% CNT | ~400 | ~35 | ~260% |
| Tecoflex 100A (0% CNT) | ~45 | ~10 | 370%*,** |
| Tecoflex 100A-25% CNT | ~1100 | ~50 | ~170% |

*did not fail in test,
**literature value

TABLE 2

Comparison of a single CNT-TPU layer sample and a multilayer laminate composed of fifteen layers thereof.

| Number of Layers | Thickness | Modulus (MPa) | Strength (MPa) | Failure Strain |
|---|---|---|---|---|
| 1 | 100 μm | 730 ± 90 | 24 ± 2 | 0.58 ± 0.1 |
| 15 (laminated) | 800 μm | 450 ± 60 | 28 ± 4 | 1.2 ± 0.8 |

Table 2 shows that lamination of multiple layers can modify the mechanical properties, in particular the modulus and the failure strain, in addition to increasing thickness. In this case, fifteen (15) layers were employed and the final thickness was less than that of the combined constituent layers prior to lamination. As there is no significant reduction in mass, the lamination step significantly decreases the porosity and hence increases the volume content of both CNTs and polyurethane.

In other cases (e.g., see Table 3) higher stiffness is observed from the densified multilayer. These exemplary cases indicate that morphological changes are dependent on both the single layer composition and the lamination conditions, in addition to a simple layering effect to increase thickness. While lamination has non-negligible effect, it is possible to tailor properties in a similar range where they provide much higher stiffness than an elastomer skin but still a high stretchability. The overall composition may be affected by pressing conditions, and lamination may also reduce the impact of roughness of the individual layers.

TABLE 3

Comparison of a single CNT-TPU layer sample with hot-press compressed and multilayer laminated versions composed of several layers thereof.

| | Density (g/cm³) | Elastic modulus (MPa) | Strength (MPa) | Failure Strain |
|---|---|---|---|---|
| Single layer | 0.76 | 460 | 25 | 0.71 |
| Single layer, pressed | 0.85 | 560 | 25 | 0.46 |
| 3-layer, laminated | 1.11 | 640 | 34 | 0.39 |
| 5-layer, laminated | 1.16 | 940 | 41 | 0.39 |

Figure 3:
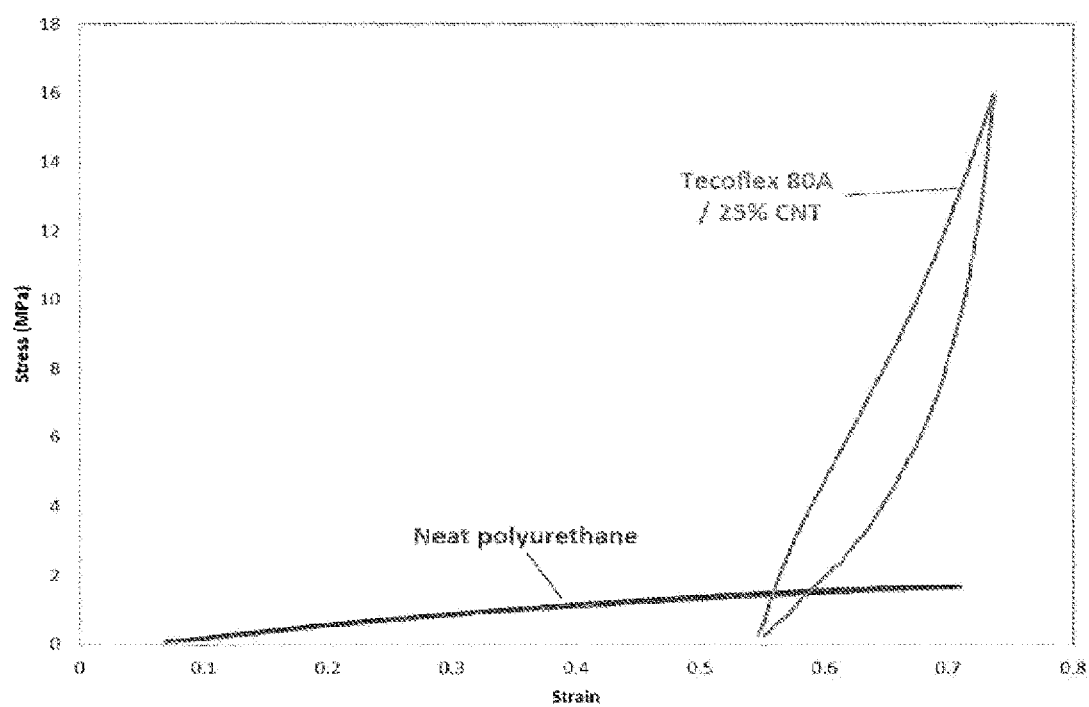
FIG. 3 is a graph showing cycling loading of a neat polyurethane sheet and a related polyurethane-modified carbon nanotube sheet.
Figure 4:
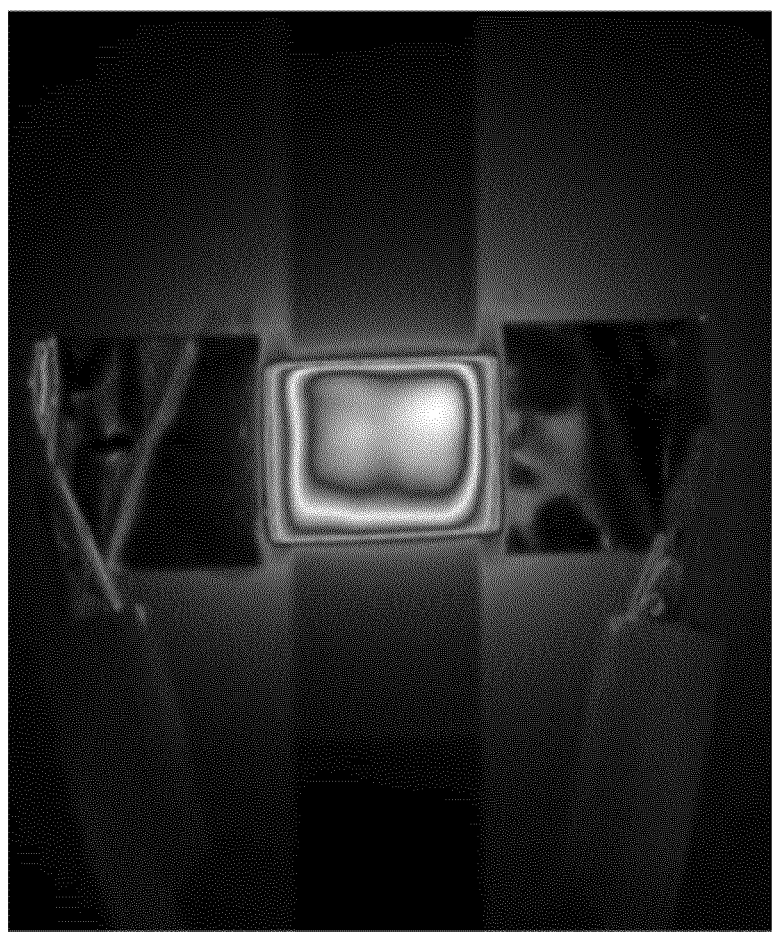
FIG. 4 is a thermal image of a powered skin material sample showing heating capacity.

Referring to FIG. 3, cyclic tests were also performed to estimate the reversible stretch capability for a non-woven polyurethane-modified CNT sheet (from Table 1) and the same type of neat polyurethane sheet. The substantially vertical loop shows reversible stretch with a modulus (slope of the line) much greater than the neat polyurethane (substantially horizontal loop). Cycling with over 20% deformation was therefore observed with greatly increased slope (higher stiffness), which confirms the nanocomposite can provide the target stretch with substantially better load carrying capacity. Based on these and similar measurements for nanotube-polyurethane composite sheets, a likely range for elastic strain and stiffness (elastic modulus) of skin material based on elastomeric polymer-modified nanotubes was established.

TABLE 4

Comparative properties for samples of skin material of about 1.5 mm in thickness and derived from the combination of a particular CNT-TPU sheet (about 0.1 mm in thickness) and a neat polyurethane layer.

| material | Tensile Modulus (MPa) | Reversible Strain (%) | Bending Modulus (MPa) |
|---|---|---|---|
| TPU sheet | 7 | 40 | 16 |
| Sandwich (CNT-TPU | TPU | CNT-TPU) | 13 | 28 | 105 |
| Sandwich (2CNT-TPU | TPU | 2CNT-PU) | 20 | 23 | 175 |
| Individual CNT-TPU layer* | 120 | 13 | NA* |

*Individual CNT-TPU layer is about 100 microns thick and too thin to measure in this bending test Referring to Table 4, in an example where polyurethane-modified CNT sheets were laminated with neat polyurethane layers to form a sandwich architecture (e.g., as seen in FIG. 7B), the bending stiffness of the skin (as represented by the modulus of elasticity in bending) is substantially increased while minimizing the increase in tensile stiffness (as represented by the tensile modulus) and hence the actuator force required to stretch the skin and structure. This skin architecture also increases the stretchability (reversible strain) in comparison to the individual NT-PU layer. Table 4 lists properties for example skin materials using this sandwich architecture.

It should be noted that the estimated ability of the resulting skin material to stretch by at least 20%, predicts for example that the skin material should provide sufficient elasticity to allow a leading edge of an airfoil to droop and to accommodate stretching with sufficient stiffness and strength for aircraft wings.

Figure 5:
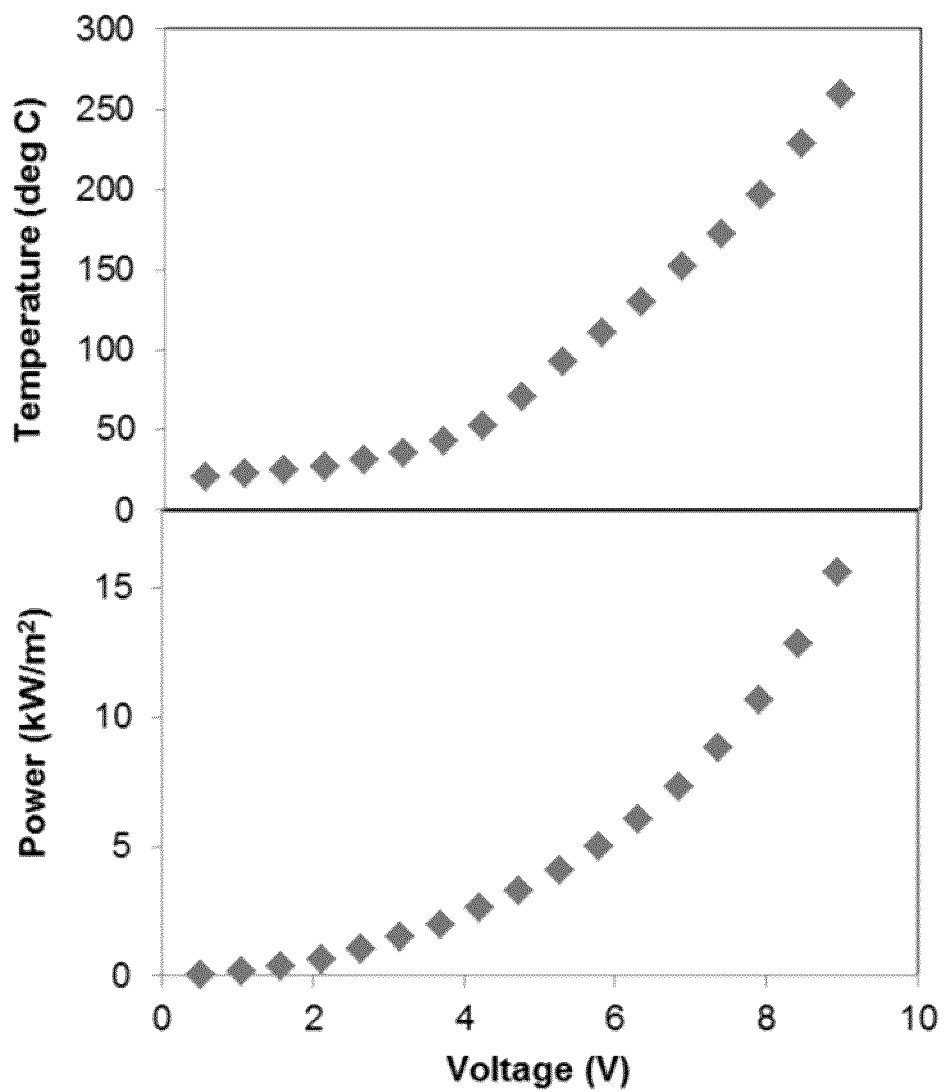
FIG. 5 includes two graphs of respective power density and temperature versus voltage which may be delivered by the ~1-inch powered skin material sample from FIG. 4.

Other experiments have been performed to validate heating capacity of the polyurethane-CNTs skin material by powering the material connected to electrodes. FIG. 5 illustrates the use of the carbon nanotube network of the skin for electrical heating. Test conditions differed from a real wing skin in terms of size and heat losses of the surroundings but the graphs from FIG. 6 however validate that power density suitable for de-icing requirements may be reached and that the skin withstands suitably high temperature. Those small voltages lead to high power density because of the small area. The experimentations demonstrate that the skin can put out high power and withstand high temperature.

Figure 8A:
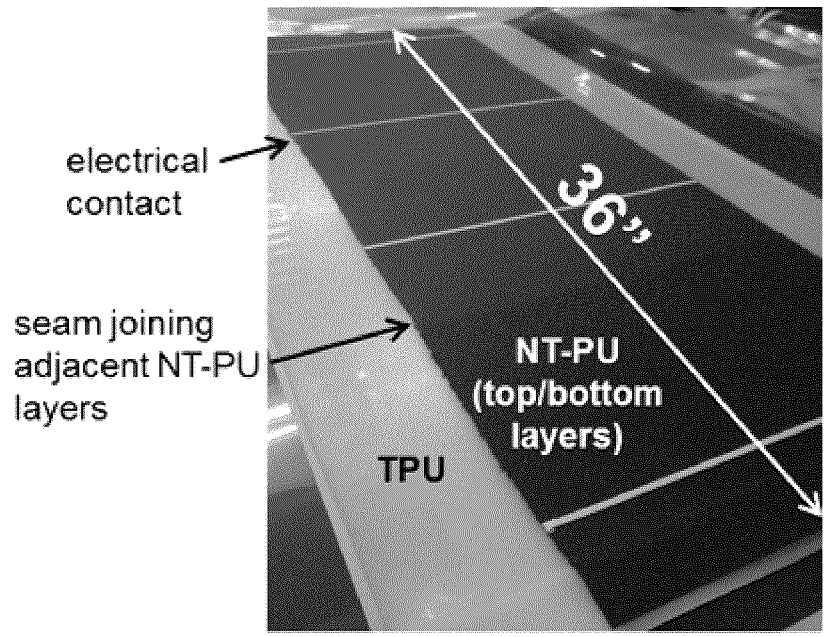
FIG. 8A is an annotated photograph of a 12"×36" skin manufactured with varied composition in both the vertical (thickness) direction and the horizontal (surface) direction immediately after lamination (before cutting away unused area of a neat polyurethane sheet).
Figure 8B:
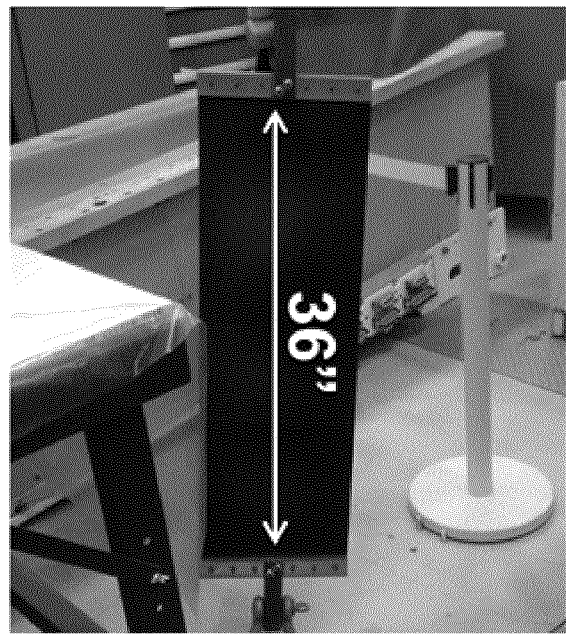
FIG. 8B is an annotated photograph of the 12"×36" skin of FIG. 8A during stretching of a full area of the skin.

FIGS. 8A and 8B illustrate a 12"×36" skin manufactured with varied composition in both the vertical (thickness) direction (neat polyurethane sheet layered between CNT-TPU nanocomposite layers) and the horizontal (surface) direction (adjacent CNT-TPU sheets joined together to make up the surface).

The invention claimed is:

1. A stretchable multiple-layer nanocomposite skin material comprising:
   a stretchable single-layer nanocomposite material sheet comprising nanotubes and an elastomeric polymer, being provided as a polymer modified nanotube network, and having a nanotube content between 5 wt % and 90 wt %, an elastomeric polymeric content between 10 wt % and 95 wt %, and a thickness between 0.005 mm and 1 mm; and
   at least one additional stretchable layer being laminated with the stretchable single-layer nanocomposite material sheet,
   wherein the skin material has a reversible stretch capacity ranging from 5 to 50% and an elastic modulus ranging from 50 MPa to 10 GPa.

2. The skin material of claim 1, wherein the network of nanotubes is provided by a non-woven sheet of nanotubes, and the nanotubes are randomly oriented within the plane of the stretchable single-layer nanocomposite material sheet.

3. The skin material of claim 1, wherein the nanotubes comprise carbon nanotubes, boron-nitride nanotubes, boron-carbon-nitrogen nanotubes, silicon-carbide nanotubes, other nanoparticles, hybrids thereof or a combination of any two or more thereof.

4. The skin material of claim 1, wherein the nanotube content of the stretchable single-layer nanocomposite material sheet is between 10 wt % and 40 wt %.

5. The skin material of claim 1, wherein the stretchable single-layer nanocomposite material sheet is a first stretchable single-layer nanocomposite material sheet and the at least one additional layer is:
   another stretchable single-layer nanocomposite material sheet comprising nanotubes differing in nature from the nanotubes of the first stretchable single-layer nanocomposite material sheet;
   another stretchable single-layer nanocomposite material sheet having a nanotube content which is different from the first stretchable single-layer nanocomposite material sheet; or
   another stretchable single-layer nanocomposite material sheet similar to the first stretchable single-layer nanocomposite material sheet.

6. The skin material of claim 1, wherein the at least one additional layer is a neat polymer layer, a composite polymer layer, or a reinforced polymer layer, including at least one elastomeric polymer.

7. The skin material of claim 1, having mechanical properties varying across a surface area thereof, and wherein at least the stretchable single-layer nanocomposite material sheet has mechanical properties varying across the surface area thereof.

8. The skin material of claim 7, having at least one of:
   a nanotube content varying across the surface area;
   a polymer content varying across the surface area;
   a nature of elastomeric polymer changing across the surface area; and
   a nature of the nanotubes changes across the surface area of the material.

9. The skin material of claim 8, wherein the nanotube content is higher in a specific area of the nanocomposite layer to enhance stiffness of the skin material.

10. The skin material of claim 8, wherein the polymer content is higher in specific area of the multiple-layer nanocomposite skin material to enhance stretchability of the skin material.

11. The skin material of claim 1, comprising a plurality of layers, wherein the number of layers varies across the surface area of the skin material.

12. The skin material of claim 1, comprising a number of layers tailored to obtain a given material thickness and a nanotube:polymer ratio tailored to provide a given stretchability profile to the skin material for application in a morphing structure or a deployable structure.

13. The skin material of claim 1, wherein the stretchable single-layer nanocomposite material sheet is a first stretchable single-layer nanocomposite material sheet and the at least one additional stretchable layer comprises:
- a second stretchable single-layer nanocomposite material sheet similar to the first stretchable single-layer nanocomposite material sheet;
- a layer of neat or reinforced elastomeric polymer comprising thermoplastic polyurethane, silicone rubber, rubber or a combination of any two or more thereof, being laminated onto the second stretchable single-layer nanocomposite material sheet; and
- a third stretchable single-layer nanocomposite material sheet similar to the first stretchable single-layer nanocomposite material sheet, being laminated onto the layer of neat or reinforced elastomeric polymer.

14. The skin material of claim 1, comprising a plurality of laminated layers tailored to obtain a material thickness between 0.05 mm and 20 mm or between 0.5 mm and 3 mm.

15. The skin material of claim 1, having a nanotube:polymer ratio tailored to provide a one-time stretch capacity of at least 100% or of at least 200%, and a stiffness of at least 50 M Pa.

16. A skin formed by direct application of the skin material as defined in claim 1 onto a support surface, wherein the nanotubes included in the material are optionally selected to provide heating, sensing, EMI shielding, neutron shielding properties or any combination of two or more thereof to the skin.

17. A morphing structure formed by direct application of a skin material as defined in claim 1 onto a support structure.

18. The morphing structure of claim 17, being at least a portion of a morphing aircraft, the morphing aircraft comprising a wing leading edge, a wing trailing edge, a tail fin, a nose cone or a combination of any two or more thereof.

19. A deployable structure produced by direct application of a skin material as defined in claim 1 onto a deployable support structure, optionally the deployable support structure is able to reversibly unfold and/or inflate resulting in stretching of the skin material.

20. A structure including a sub-structure and a skin as defined in claim 16, wherein the skin forms at least part of an outer surface of the structure by application onto the sub-structure.

* * * * *